United States Patent [19]

Wilde et al.

[11] Patent Number: 5,496,802
[45] Date of Patent: Mar. 5, 1996

[54] CONTROL OF MILK SECRETION

[75] Inventors: Colin J. Wilde; Malcolm Peaker, both of Alloway; Caroline V. P. Addey, Ayr, all of Scotland

[73] Assignee: British Technology Group Ltd, London, England

[21] Appl. No.: 140,183

[22] PCT Filed: May 10, 1991

[86] PCT No.: PCT/GB91/00744

§ 371 Date: Nov. 8, 1993

§ 102(e) Date: Nov. 8, 1993

[87] PCT Pub. No.: WO92/20714

PCT Pub. Date: Nov. 26, 1992

[51] Int. Cl.$^6$ .......................... C07K 14/00; C07K 16/06; C07K 16/18; A61K 38/17
[52] U.S. Cl. .............. 514/2; 530/300; 530/350; 530/365; 530/366; 530/386; 530/387.1; 530/388.2; 530/395; 530/416; 530/832; 530/833; 530/861; 530/863; 530/864; 514/12; 424/198.1
[58] Field of Search ...................... 530/300, 350, 530/365, 366, 386, 387.1, 388.2, 395, 416, 832, 833, 861, 863, 864; 514/2, 12; 424/198.1

[56] References Cited

FOREIGN PATENT DOCUMENTS

WO9107439 5/1990 WIPO.
WO9107434 5/1991 WIPO.

OTHER PUBLICATIONS

Prentice et al. Biochemical Society Transactions Apr. 1989 p. 122.
Wilde et al. Biochimica Biophysica Acta. 992: 315–319 1989. I.
Hill et al. Can Inst. Food Scien. Tech. 19: 5 227–230 1986.
Wilde et al II, Quarty Journal of Experimental Physiology 73 391–397 1988.
Goding Monoclonal Antibod. Principles and Practice, 1986, Academic Press p. 59.

*Primary Examiner*—Lila Feisee
*Attorney, Agent, or Firm*—Nixon & Vanderhye

[57] ABSTRACT

A protein which inhibits milk secretion by lactating cows and which is present in the eighth (6B, Figure) significant peak when a nominally 10–30 KDa fraction of the whey proteins of the milk is resolved on a "Mono Q" anion exchange column using 10 mM imidazole buffer, pH 7.0 and a sodium chloride elution gradient.

5 Claims, 1 Drawing Sheet

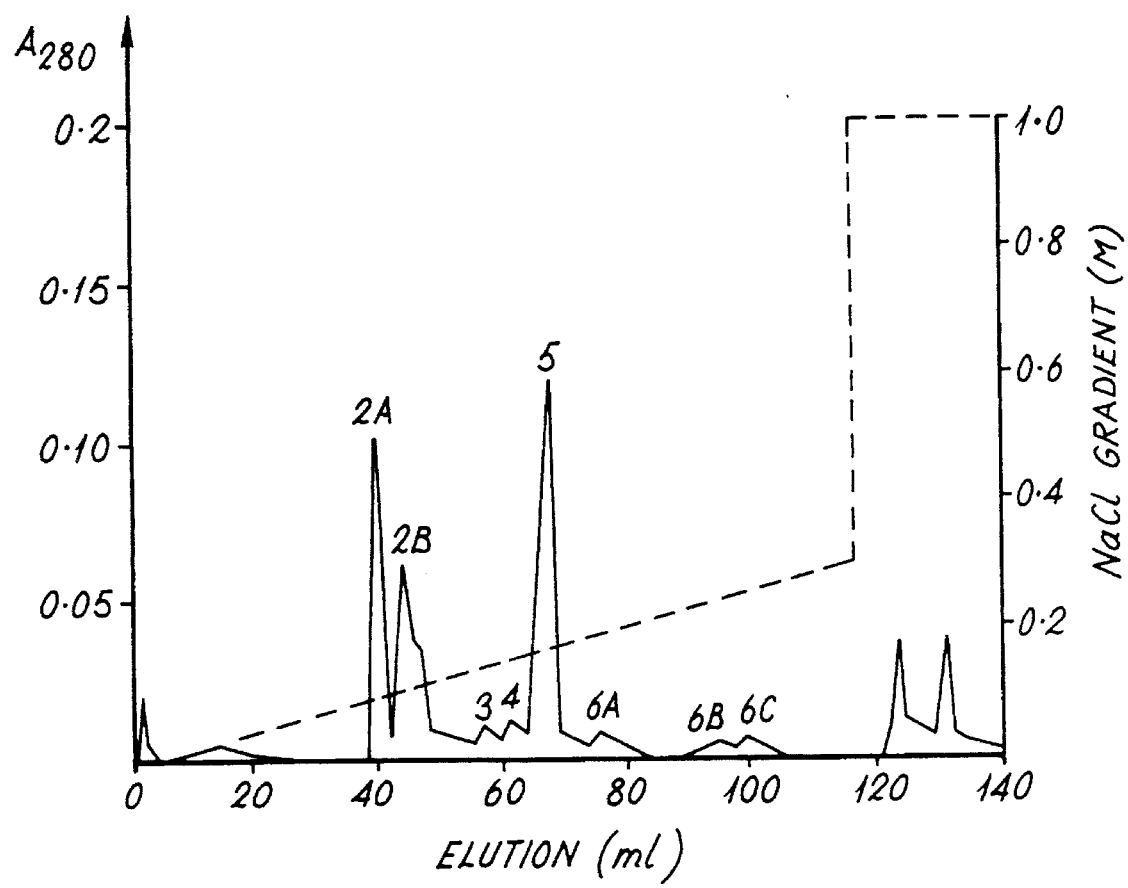

CONTROL OF MILK SECRETION

BACKGROUND OF THE INVENTION

1. Field of the invention

This invention relates to a newly isolated protein from cow's milk and the use of the protein or antibodies thereto for the control of milk secretion in lactating animals.

2. Description of the Prior Art

The rate of milk secretion by a lactating animal is regulated by the frequency of milk removal. In other words, there Is a mechanism which acts to match the animal's supply of milk to the demand of her offspring or of a farmer's milking regime. Part of this control is achieved by the release of galactopoietic hormones during suckling or milking. However, studies by workers at the Hannah Research Institute, Ayr, Scotland on lactating goats have shown that another factor is involved. This is an inhibitor which decreases milk secretion at a local level, i.e. at the individual gland of an udder.

It has already been shown that the inhibitor is present in a goat milk fraction containing whey proteins of molecular weight 10–30 KDa, this range of molecular weights being determined by the nominal sizes of filters used in ultrafiltration of the whey. The effect has been demonstrated both in vitro and in vivo. The in vitro technique, described by C. J. Wilde et al., Biochem. J. 242, 285–288 (1987), consists in culturing explanted pieces of rabbit mammary with and without the milk fraction and demonstrating the inhibition of lactose and casein synthesis. See also G. M. Stewart et al., J. Endocrinology 118, R1–R3 (1988). In the vivo technique, C. J. Wilde et al., Quarterly Journal of Experimental Physiology 73, 391–397 (1988), the milk fraction was injected into a single mammary gland of goats via the teat canal. A temporary dose-dependent reduction of milk yield, specific to that gland, was observed.

It has remained a problem to determine whether an inhibitor is present in cow's milk and, if so, to purify it sufficiently for identification, with a view to chemical or biological synthesis.

REFERENCE TO UNPUBLISHED PRIOR PATENT APPLICATIONS

Our unpublished U.K. Patent Application 9024653.9 entitled "CONTROL OF MILK SECRETION", filed 13th Nov. 1990, claiming priority of U.K. Patent Application 8925594.7 filed 13th Nov. 1989, describes and claims a protein isolated from the 10–30 KDa (nominal) fraction of whey proteins of goat's milk and having an inhibitory effect on milk secretion. This protein has a molecular weight (by gel filtration chromatography) of about 7.6 KDa and is present in the third significant peak when a said fraction is resolved on a defined anion exchange column under defined conditions. There are corresponding patent applications of the same date and priority in the PCT (GB90/01742), Ireland (90/4086) and New Zealand (236054).

Our companion unpublished U.K. Patent Application 9024649.7 entitled "CONTROL OF SECRETION OF MILK", filed 13th Nov. 1990, claiming priority of U.K. Patent Application No. 8925595.4 filed 13th Nov. 1989, describes and claims a protein isolated from the 10–30 KDa (nominal) fraction of whey proteins of cow's milk and having an inhibitory effect on milk secretion. This protein has a molecular weight (by gel filtration chromatography) of about 7 KDa and is present in the second significant peak (designated peak "2A") when a said fraction is resolved on a defined anion exchange column under defined conditions. There are corresponding patent applications of the same date and priority in the PCT (GB90/01743), Ireland (90/4087) and New Zealand (236051).

SUMMARY OF THE INVENTION

It has now been found that inhibitory activity towards milk secretion is also present in the eighth significant peak (6B) when a said fraction of cow's milk whey proteins is resolved under the same conditions as referred to above.

There are various ways of defining the protein of the invention, of varying degrees of reliability. One currently preferred definition is a protein which inhibits milk secretion by lactating cows and which is present in the eighth significant peak (6B) when a nominally 10–30 KDa fraction of the whey proteins of the milk is resolved on an anion exchange column using 10 mM imidazole buffer, pH 7.0 and a sodium chloride elution gradient. The column is composed of particles of mono-disperse hydrophilic polymer having pendant —$CH_2N(CH_3)_3^+$ groups, the particle diameter being 10+0.5 μM.

The protein of the invention can optionally be further defined as follows. It has a molecular weight, as determined by gel filtration chromatography of the product of the 6B peak, without further purification, is about 6.5. Its isoelectric point in a polyacrylamide gel is within the range 5.1 to 5.4.

The protein of the invention can optionally further be defined by reference to its having a shared epitope with the milk secretion-inhibitory bovine 2A protein of our second above-mentioned prior application. This was demonstrated by raising a mouse monoclonal antibody by a conventional technique against the milk secretion-inhibitory goat peak 3 protein of our first above-mentioned prior application and testing its reactivity with the products of various bovine peaks. It was found that the anti-(goat 3 peak) monoclonal antibody reacted with the product of bovine peak 2 (equivalent to the combined product of peaks 2A and 2B), and also with peak 2A, but not with the products of at least the fifth and sixth peaks 4 and 5). It is either only weakly reactive or non-reactive with the fourth, seventh and ninth bovine peaks (3, 6A and 6C), thus indicating that this is a monoclonal antibody of high specificity for the bovine milk secretion-inhibitory proteins 2A and 6B.

Any combination of one or more of the above features, together with the inhibitory action of the protein, might be sufficient to define the protein uniquely and accordingly applicant does not wish to be limited unnecessarily to specific combinations, in case one of them or some aspect of one of them might later be re-determined and found not sufficiently to approximate to their definition given above, while the remaining features are confirmed, and leave no doubt as to the identity of the protein. Precisely which features are the most meaningful and the most reliable are, in any case, a matter of judgement, the preferred definitions given above reflecting applicant's current judgement. It will be appreciated, therefore, that the protein defined by other combinations of features herein set forth is to be considered as encompassed by the invention.

The protein can be in glycosylated or unglycosylated form.

Antibodies to the protein, whether polyclonal, monoclonal or engineered, are within the scope of this invention.

Where national patent law permits, the administration of the inhibitor to decrease milk yield or an antibody thereto to suppress at least partly the action of the inhibitor, to cows or other animals is within the invention.

BRIEF DESCRIPTION OF THE DRAWING

The Figure shows the resolution of the 10–30 KDa fraction by anion-exchange chromatography;

DESCRIPTION OF THE PREFERRED EMBODIMENTS

The protein of the invention exists in cow's milk, probably in glycosylated form. It is believed that the effect of glycosylation is simply for attachment of the protein to the appropriate cells within the mammary gland. It would be expected, therefore, that the protein could be administered locally to the gland in an unglycosylated form.

In relation to goat's milk, using a 10–30 KDa fraction of whey protein, it has been demonstrated that the inhibition of lactose and casein synthesis in mammary explant culture is dependent on the dose of the inhibitor-containing fraction. Further, when the explants have been exposed to the inhibitor-containing fraction, washed and re-cultured in fresh medium in the absence of the inhibitor, the capacity to synthesise lactose and casein is recovered. In vivo, it is found that administration of the protein to the mammary gland causes the milk yield to decrease within hours, with full recovery of yield 24–36 h after a single administration. However, when a change in milking frequency—and therefore autocrine control— was sustained over weeks, there was an effect on the synthetic capacity i.e. degree of differentiation of the secretory cells attributable to the autocrine inhibitor. These long-term effects on mammary cell activity are accompanied by changes in the number of cell-surface hormone receptors for prolactin. Thrice-daily milking of lactating goats for 4 weeks increases cell activity and prolactin receptor number per cell, whereas a decrease in milking efficiency extending over 21 weeks reduces secretory cell differentiation and prolactin receptor number. Therefore, these long-term effects, and also the acute regulation by the autocrine inhibitor of the invention could be due primarily to modulation of the sensitivity of individual glands to endocrine control. There is every reason to believe that the same effects will be demonstrable in relation to the protein of the invention obtained from cow's milk, in relation to cows.

Antibodies can be raised against the protein of the invention by any conventional methods, e.g. as polyclonal antisera, mouse monoclonal antibodies, cow-mouse hybrid monoclonal antibodies or as engineered antibodies, by any of the currently available methods. Passive immunisation methods can then be used to generate a reduction in the effect of the natural inhibitor, when this is desired in order to increase milk yield. Frequently, however, there will be a need to reduce milk yield in order to meet milk quotas, in which event the inhibitor itself is administered. Conventional carriers and adjuvants known in vaccination can be used.

The invention is applicable to any animal responsive to the inhibitor defined herein. Since the 10–30 KDa goat's milk fraction has been successfully found to reduce milk accumulation and relevant enzyme activities when injected into the mammary gland of rabbits, it is likely that the cow's milk inhibitor will be effective in some other lactating animals.

For intraductal injection into the mammary gland, a dose in the range of 1 to 50 mg, especially 5 to 20 mg of inhibitor, is likely to be effective and should be repeated as required, e.g. daily, and possibly reduced when given over long periods.

The protein of the invention can be obtained from cow's milk by the method described in the Example or some variant thereon or addition thereto, e.g. chromatofocussing as described in our second above-mentioned prior application. It can be recovered in pure form from an eluate by extensive dialysis against water (using an appropriate membrane for retention of the protein, e.g. with a nominal molecular weight cut-off of about 6 KDa) and freeze-drying. However, it is expected that it would be synthesised by protein synthesis or by a recombinant DNA method.

The following Example illustrates the invention.

EXAMPLE

This Example describes the preparation and properties of the inhibitor of the invention.

1. Preparation of cow milk fractions

Milk was obtained at the morning milking from Friesian cows, and was defatted by centrifugation (2500 g, 15° C., 20 min) and filtered through glass wool. Defatted milk was centrifuged for 2 h at 15° C., yielding a pellet of casein micelles and a clear supernatant containing whey proteins. The whey fraction was dialysed against distilled water for 24 h.

The whey fraction was subjected to ultrafiltration using a filter with a nominal cut-off value of molecular weight 30,000 Daltons (Da). The filtrate obtained with the 30,000 Da filter was concentrated by ultrafiltration with a 10,000 Da filter. The 10,000–30,000 Da fraction was dialysed extensively against water, sterilized by filter sterilization and concentrated by freeze-drying for anion exchange chromatography.

2. Anion exchange chromatography of cow whey proteins

The 10–30 KDa whey fraction was resolved on a "MonoQ HR 10/10" anion exchange column (Pharmacia) using an "FPLC" chromatography system (Pharmacia). The whey fraction was dissolved in 10 mM imidazole at four times its concentration in the original milk and the pH adjusted to 7.0. Before chromatography, the sample and buffer (degassed) were filtered through 0.2 mm filters. 1 ml of the 4× concentrated whey fraction was loaded for each separation; the flow rate was 4.0 ml/min. A sodium chloride elution gradient was used.

Fractions containing protein peaks eluted from the column were dialysed extensively against distilled water, freeze-dried and stored at −20° C., before use in the next stage.

The sole Figure of the drawing shows the elution of protein from the chromatography column. Protein concentration, as absorption of light at 280 nm, on the left-hand ordinate is plotted against cumulative volume of eluted material on the abscissa. The plot is shown as lines. The right-hand ordinate is calibrated to show the sodium chloride gradient, from 0 to 1.0M, used in the eluant. The broken line is a plot of the sodium chloride concentration. The peaks are labelled Vo=void volume containing material not bound by the column and then in order of elution, the peaks being numbered as far as possible by a system which relates them to those obtained when the non-ultrafiltered whey protein is chromatographed by the same method. The numbering is 1, 2A, 2B 3, 4, 5, 6A, 6B, 6C. (There are two further peaks, which do not correlate with those for the non-ultrafiltered whey).

3. Mammary explant into bioassay of milk fractions

Mammary tissue was cultured as explants, small pieces of parenchymal tissue approximately 1 cm³ and weighing 0.5–0.7 mg. Explants were prepared from mammary tissue of mid-pregnant New Zealand White rabbits as described by R. Dils & I.A. Forsyth in Methods in Enzymology 72, 724–742 (1981). The explants were cultured in a defined culture medium (Medium 199; Gibco Europe Ltd., Paisley, UK) on stainless steel grids each holding 30 explants, so that the explants were in contact with the medium but not completely submerged in it. The medium was supplemented throughout with insulin (5 mg/ml), cortisol (100 ng/ml) and prolactin (1 mg/ml). Explants were cultured in this medium under an atmosphere of air/$CO_2$ (19:1 v/v) for 42 h, with replenishment of medium after 24 h. At this time, groups of explants (3 or 4 groups per treatment) were transferred into fresh medium containing hormones and one of the fractions of cow milk under test. The milk fractions tested in this experiment were obtained from cow's milk whey which had not been ultrafiltered (as distinct from the 10–30 KDa fraction referred to above), but which had been fractionated by anion exchange chromatography as described above. They were dissolved in 10 mM Heres, pH 7.4, at twice their concentration in the original milk, and added to an equal volume of two times concentrated culture medium, so as to be at 100% of their original milk concentration in normal strength culture medium. Control cultures, containing only the diluent for the milk fractions, were included in each experiment. Average rates of lactose and casein synthesis during a further 6 h culture in the presence or absence of milk fraction were measured by the addition of [U-$^{14}$C] glucose (U=uniformly labelled; 0.18 mCi/mmol) and L-[4, 5-$^3$H]leucine (2.22 mCi/mmol) respectively in this culture medium. At the end of the 6 h period, explants and culture medium were separated and stored frozen in liquid nitrogen.

Explants were homogenized at 4° C. in 1.0 ml of 10 mM Tris/HCl, pH 7.0, containing 5 mM ethyleneglycol-bis-(2-aminoethyl ether) N,N,N',N'-tetraacetic acid (EGTA) and 2 mM phenylmethanesulphonyl fluoride by 10 strokes with a glass/PTFE homogenizer, followed by sonication for 30 s. (Kontes ultrasonic cell disruptor, 30% maximum power), and a particle-free supernatant was prepared by centrifugation at 10,000 g for 5 min. $^3$H-labelled casein was prepared from the particle-free supernatant by precipitation at its isoelectric point, and the precipitate was subjected to SDS-polyacrylamide gel electrophoresis, as described by C. J. Wilde et al., Exp. Cell Res. 151, 519–532 (1984). Bands corresponding to casein polypeptides were visualized by staining with Coomassie brilliant blue, and were excised and counted for [$^3$H] radioactivity as described by S. M. Russell et al., Biochim. Biophys. Acta 714, 34–45 (1982). [$^{14}$C] lactose was selectively precipitated from explant homogenates and culture medium using ethanol/diethyl ether (3:1, v/v), N. J. Kuhn & A. Nhite, Biochem. J. 148, 77–84 (1975) and the radioactivity of the precipitate counted. Results were corrected for carry-through of [$^{14}$C] glucose from culture medium (usually <0.08%), by measuring [$^{14}$C] radioactivity after extraction of uncultured medium. The addition of milk fractions did not affect the distribution of secreted products between the extracellular space of the explants and the medium.

The amount of radioactive material (casein and lactose) was expressed as a percentage of that produced by the explants to which no milk fraction had been added. The results are shown in Table 1. The figures in parenthesis are the numbers of experiments performed on the various peaks.

TABLE 1

| Peak number | Lactose synthesis (% of control) | Casein synthesis (% of control) |
|---|---|---|
| No addition (control) | 100 | 100 |
| 1 | 96.8 ± 3.7 (5) | 90.6 ± 3.5 (5) |
| 2 (=2A + 2B) | 65.8 ± 7.5 (6)* | 63.1 ± 14.2 (6)* |
| 3 | 94.6 ± 4.6 (5) | 86.7 ± 12.2 (5) |
| 4 | 104.0 ± 6.0 (5) | 146.4 ± 22.8 (5) |
| 5 | 102.1 ± 1.7 (4) | 94.3 ± 21.3 (5) |
| 6 (=6A + 6B + 6C) | 69.9 ± 10.1 (5) | 75.9 ± 15.3 (6) |
| 7 | 85.3 ± 9.8 (4) | 91.6 ± 19.8 (5) |
| 8 | 90.4 ± 4.8 (3) | 94.4 ± 6.1 (5) |
| 9 | 110.9 ± 5.6 (3) | 90.3 ± 10.8 (4) |
| 10 | 102.0 (2) | 120.3 (2) |

*Test vs control; p < 0.05 (paired t-test)

The above experiments were then repeated, using fractions from peaks 6A, 6B, and 6C separately, with the results shown in Table 2 below.

TABLE 2

| Peak number | Lactose synthesis (% of controls) | Casein synthesis (% of controls) |
|---|---|---|
| No addition (control) | 100 | 100 |
| 6A | 77.1 ± 18.8 | 107.2 ± 17.4 |
| 6B | 56.6 ± 5.0 | 62.6 ± 15.9 |
| 6C | 84.2 ± 12.1 | 95.7 ± 20.3 |

Results are the mean ± s.e.m. for 3 experiments.

It will be seen that all the fractions were inhibitory to some extent, particularly 6B, although lack of clear separation of the inhibitor component between peaks 6A, 6B and 6C doubtless accounts for some of these effects.

4. Gel filtration chromatography of peaks

Gel filtration of each of peaks 6A, 6B and 6C prepared from the 10–30 KDa fraction as described above was carried out using an "FPLC" chromatography system and a "Superose 12 HR 10/30" column (Pharmacia). "Superose 12" is a highly cross-linked agarose matrix with a particle size of 10±2 mm and an exclusion limit of $2\times10^6$ Da. The buffer was 50 mM Tris/HCl , pH 7.5 containing 100 mM KCl, which was filtered (0.2 mm filter) and degassed before use. Samples (routinely 1–10 mg in a maximum volume of 200 ml) were dissolved in the same buffer and filtered before use (0.2 mm filter). The column was calibrated using molecular weight standards in the m.w. range 200,000–12,400 (Sigma MW-GF-200 kit) and also aprotinin (molecular weight 6,500) and bovine a-lactalbumin (molecular weight 14,200). Calibration curves of log[molecular weight] versus $V_e/V_o$ were prepared, where $V_o$=void volume and $V_e$=elution volume of each protein. $V_o$ was determined using Dextran Blue (Sigma; approximate molecular weight 2,000 KDa). Peak 6A contained a major peak of m.w 12,500 KDa plus other less well defined constituents, 6B eluted as one major peak with m.w 6,500 KDa and peak 6C as two components of m.w. 12,500 and 6,500 KDa.

5. Isoelectric focussing of peak 6B protein

Isoelectric focusing was performed using the Pharmacia "PhastGel" electrophoresis system. The method used "PhastGel IEF 4–6.5". "Phastgel IEF" media are homogeneous polyacrylamide gels containing "Pharmalyte" carrier ampholytes. "Pharmalyte" generates stable, linear pH gradients in the gels during electrophoresis, in this case in the pH range 4 to 6.5. Proteins migrate under an electric field, essentially unhindered by the porous gel, to a point in the pH gradient that corresponds to their pI (isoelectric point).

The sample, 1 µg, of peak 6B, which had been extensively dialysed against distilled water, was applied to one well of the gel; "Pharmacia pI Calibration Kit" proteins were applied to wells on both sides of the sample well. The resulting protein bands were visualised by staining with Coomassie blue after electrophoresis. Peak 6B gave rise to a single protein band corresponding to pI 5.2–5.3.

6. Cross-reaction of peak 6B with a monoclonal antibody against the goat inhibitor that also recognises bovine peak 2A.

Female balb/c mice were immunised with a goat milk protein fraction containing a feedback inhibitor of milk secretion (see the first above-mentioned prior application). The inhibitory milk protein fraction, designated peak 3, was prepared by anion-exchange chromatography of a 10–30 KDa fraction of goat whey proteins on a Pharmacia FPLC (Fast Protein Liquid Chromatography) HR 10/10 Mono-Q column. The elution buffer was 20 mM bis tris propane pH 7.0, and proteins were separated using a sodium acetate gradient. Peak 3 was dialysed extensively against water, freeze-dried and stored at −20° C. until required.

For immunisation, peak 3 was conjugated to bovine serum albumin (BSA) by glutaraldehyde treatment. Thus, peak 3 (100 µg) dissolved in 0.1M- sodium phosphate buffer pH 6.8 was mixed with 100 µg BSA and 0.001% (w/v) glutaraldehyde at room temperature for 1 h. After addition of lysine (final concentration 25 mM) and a further 2 h at room temperature, the conjugated protein was dialysed against water and freeze-dried.

Mice were immunised by subcutaneous injections of goat inhibitor-BSA conjugate (each containing 50–100 µg of inhibitor protein) until an antibody titre of greater than 1/1000 was obtained by ELISA. A final intraperitoneal booster of 100 µg was given 4 days prior to cell fusion. The methods for cell fusion and preparation of monoclonal antibody were as described by Campbell in "Monoclonal antibody technology" (Burton, R. H. & Van Knippenberg, P. H., eds.), Elsevier Science Publishers, Amsterdam, 1984, Chapter 6 pp. 120–133. Briefly, mouse spleen cells were fused with the mouse myeloma cell line Y63-Ag-653 at a ratio of 10:1 spleen:myeloma cells. Cells were fused with 50% polyethylene glycol 1500. Hybridomas were grown in RPMI medium and 207. (v/v) foetal calf serum containing hypoxanthine, aminopterin and thymidine (HAT medium). The fused cells were incubated at 37° C. in a humidified $CO_2$ incubator. After one week, cells were fed with fresh HAT medium. After unfused myeloma cells and spleen cells had died, hybridomas were fed with HT medium i.e. HAT minus aminopterin, and the foetal calf serum concentration was gradually reduced to 10% (w/v).

Clones were screened for antibody production by an ELISA-based method 14–20 days after cell fusion, using bovine peak 2 (=2A+2B of our second above-mentioned prior application) obtained by anion-exchange of a 10–30 KDa cow's milk whey protein fraction as described in our second above-mentioned prior application. Positive clones were sub-cloned twice by limiting dilution, and the resultant monoclonal cells were tested to determine the specificity of the secreted antibody. In tests using protein fractions obtained by anion-exchange chromatography, the antibody gave a strong positive reaction with peak 2 (which contains the inhibitor) and peak 6B. When peak 2 components were tested individually, the antibody recognised 2A (containing the inhibitor) to a greater extent than 2B. Weak cross-reactivity was observed with peaks 3, 6A and 6C, but in each case this was ascribable to contamination of these fractions with peak 2 or peak 6B. The antibody did not recognise peaks 4 or 5, which together constitute the major fraction of proteins in the 10–30 KDa whey fraction. The results indicate that a monoclonal antibody showing specificity for the bovine feedback inhibitor cross-reacts with the protein designated 6B. This suggests that there are structural similarities between these proteins, as well as a common ability to inhibit milk synthesis by rabbit mammary explants in tissue culture.

We claim:

1. An isolated protein in glycosylated or unglycosylated form which inhibits milk secretion by lactating cows and which is present in the eighth significant peak, shown on the drawing as "6B", when a fraction of the whey proteins of the milk separated by ultrafiltration using filters of cut-off values 10 KDa and 30 KDa, is resolved on an anion exchange column of particles of monodisperse hydrophilic polymer having pendant —$CH_2N(CH_3)_3^+$ groups, the particle diameter being 10±0.5µm, using 10 mM imidazole buffer, pH 7.0 and a sodium chloride elution gradient of 0 to 1.0M and said protein having a molecular weight, as determined by gel filtration chromatography, of about 6.5 KDa, and an isoelectric point determined by isoelectric focussing of material from said peak 6B in a polyacrylamide gel on the product of the 6B peak within the range 5.1 to 5.4.

2. A protein according to claim 1 further defined in that it reacts with a mouse monoclonal antibody raised against the product of the third significant peak when a fraction of the whey proteins of goat's milk, separated by ultrafiltration using filters of cut-off values 10 KDa and 30 KDa, is resolved on a said anion exchange column, using 20 mM bis tris propane buffer, pH 7.0 and a sodium acetate gradient of 0 to 1.0M, said monoclonal antibody also being reactive with second significant peak, shown in the drawing as peak "2A", but being non-reactive with the products of at least the fifth and sixth peaks, shown in the drawing as peaks "4" and "5", when said fraction of whey protein of cow's milk is resolved under the conditions defined above for cow's milk proteins.

3. An isolated antibody raised against the isolated protein of claim 1.

4. A method of reducing the milk yield of a cow, which comprises administering to said cow the protein of claim 1.

5. A method of reducing the milk yield of a cow, which comprises administering to said cow the protein of claim 2.

\* \* \* \* \*